United States Patent
Hui

(10) Patent No.: US 9,833,163 B2
(45) Date of Patent: Dec. 5, 2017

(54) MICROCURRENT DEVICE FOR THE DETECTION OF TISSUE INJURY

(71) Applicant: Timothy En-Pu Hui, Los Angeles, CA (US)

(72) Inventor: Timothy En-Pu Hui, Los Angeles, CA (US)

(*) Notice: Subject to any disclaimer, the term of this patent is extended or adjusted under 35 U.S.C. 154(b) by 0 days.

(21) Appl. No.: 14/250,401

(22) Filed: Apr. 11, 2014

(65) Prior Publication Data

US 2016/0183837 A1     Jun. 30, 2016

Related U.S. Application Data

(60) Provisional application No. 61/814,665, filed on Apr. 22, 2013.

(51) Int. Cl.
| | |
|---|---|
| *A61B 5/053* | (2006.01) |
| *A61B 5/00* | (2006.01) |
| *A61B 90/00* | (2016.01) |

(52) U.S. Cl.
CPC ........ *A61B 5/053* (2013.01); *A61B 2090/065* (2016.02)

(58) Field of Classification Search
CPC ....................................................... A61B 5/053
See application file for complete search history.

(56) References Cited

U.S. PATENT DOCUMENTS

| | | | | |
|---|---|---|---|---|
| 2004/0082850 A1* | 4/2004 | Bonner | ................... | A61B 5/06 600/424 |
| 2006/0155220 A1* | 7/2006 | Oslay | .................... | A61N 1/322 601/21 |
| 2006/0216251 A1* | 9/2006 | Morariu | ................... | A61K 8/41 424/59 |
| 2008/0287750 A1* | 11/2008 | Hashimshony | .......... | A61B 5/00 600/301 |
| 2010/0036209 A1* | 2/2010 | Ferren | .................. | A61B 5/0002 600/301 |
| 2010/0222696 A1* | 9/2010 | Feldkamp | ............ | A61B 5/0522 600/547 |
| 2013/0035606 A1* | 2/2013 | Wichner | .............. | A61B 5/7203 600/546 |

OTHER PUBLICATIONS

Smith, G. B., et al. "Predicting successful brachial plexus block using changes in skin electrical resistance." British journal of anaesthesia 60.6 (1988): 703-708.*

* cited by examiner

*Primary Examiner* — Michael C Stout
*Assistant Examiner* — Nicholas E Kolderman
(74) *Attorney, Agent, or Firm* — Ingenium Patents LLC; Peter R. Kramer

(57) ABSTRACT

This invention detects tissue injury by measuring decreased skin conductance as shown by research. Two electrical probes on the device are placed onto a subject's skin. The device sends an electrical microcurrent from one probe, through the subject's skin, to the other probe. A gauge measures the microcurrent in microamps, and a speaker emits a tone with pitch and volume proportional to the percentage of maximum conductance. Per research, the skin conductance will decrease significantly over a site of tissue injury, such as an average of around 70% over a sprained ankle. Also, force gauges measure the force applied to the electrical probes for consistency of measurement. Cotton pads are placed at the tips of the electrical probes for hygiene.

2 Claims, 5 Drawing Sheets

MICROCURRENT DEVICE FOR THE DETECTION OF TISSUE INJURY

BACKGROUND OF THE INVENTION

Field of the Invention

This disclosure describes inventive embodiments in the field of detection of soft tissue injuries of muscles, fascia, ligaments, and tendons.

Description of the Related Art

Medical devices which specifically and objectively detect soft tissue injury, that is injury of muscles; fascia, ligaments, tendons, and other non-bone structures have not been previously disclosed.

Other diagnostic tests can objectively detect soft tissue injury, but they do so indirectly. MRIs, diagnostic Ultrasound, x-rays, and CT scans can detect edema that occurs secondary to a soft tissue injury, provided that there is a sufficient amount of edema from the injury. However, no simple, fast, low-cost, direct method has been previously disclosed to detect soft tissue injury.

MRI and other imaging instruments are very expensive, slow, and require a lot of training to properly use. Also, they detect many different conditions, and soft tissue injury is something only detected through edema or ruptured tissue. Tissue injury is not directly detected.

BRIEF SUMMARY OF THE INVENTION

The inventive subject matter described herein includes apparatuses and methods to detect soft tissue injury, that is injury of muscles, fascia, ligaments, tendons, and most other non-bone structures. The apparatus works by pairing electronic and mechanical components to detect and measure the severity of soft tissue injury. The apparatuses and methods of the invention measure microcurrent applied through the skin between two probes. Force gauges permit consistent pressure when probes are applied to the skin. The magnitude of measured microcurrent is inversely related to the degree of tissue injury. Thus, the apparatus and method permit rapid and cost efficient assessment of soft tissue injury.

LISTING OF REFERENCE NUMERALS IN THE DRAWINGS

Figure 1:
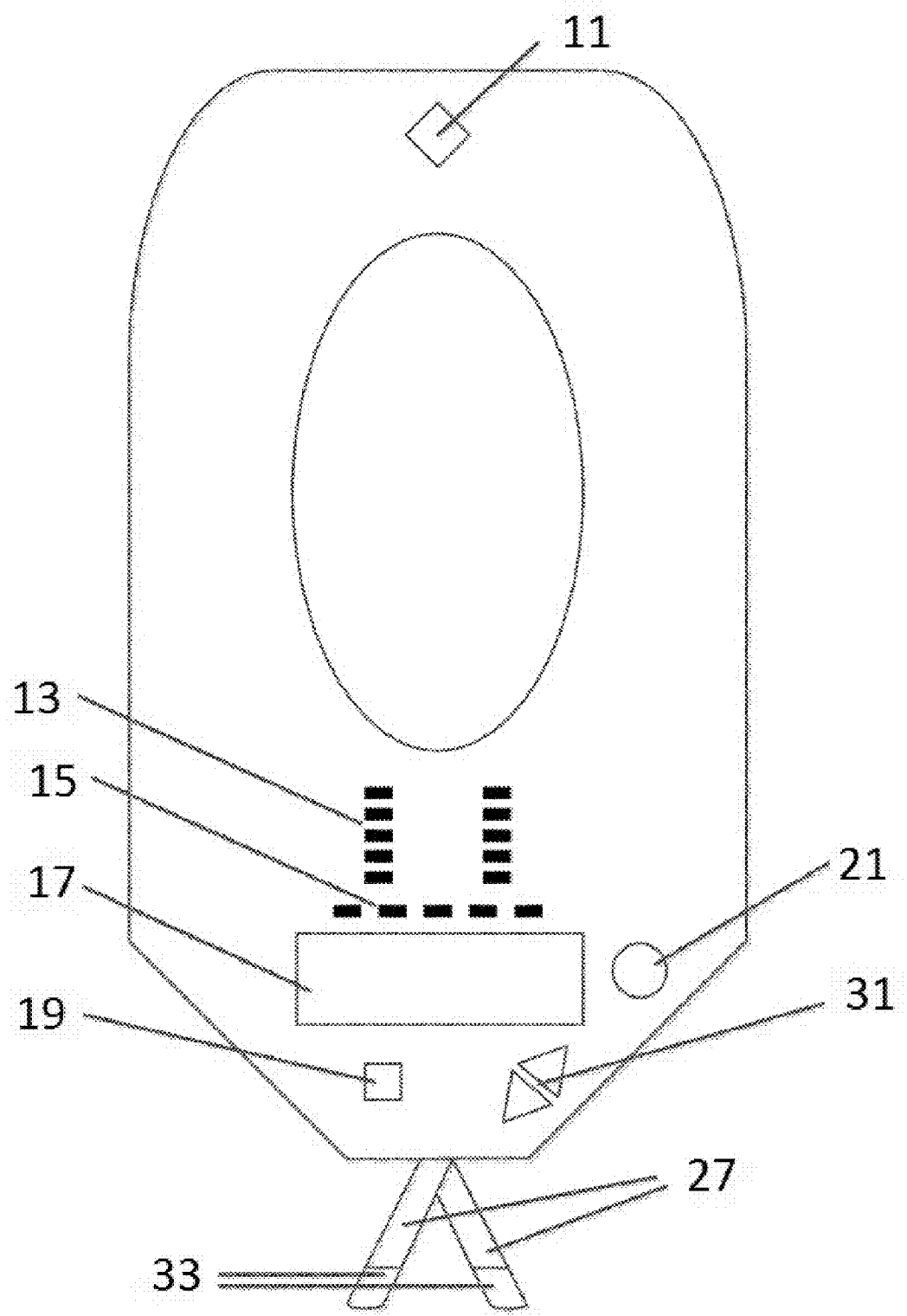
FIG. 1—Schematic front view of an embodiment
FIG. 2—Schematic internal view of some components within an embodiment
FIG. 3—Perspective view of an embodiment
FIG. 4—Side view of an embodiment
FIG. 5—Rear view of an embodiment
Figure 2:
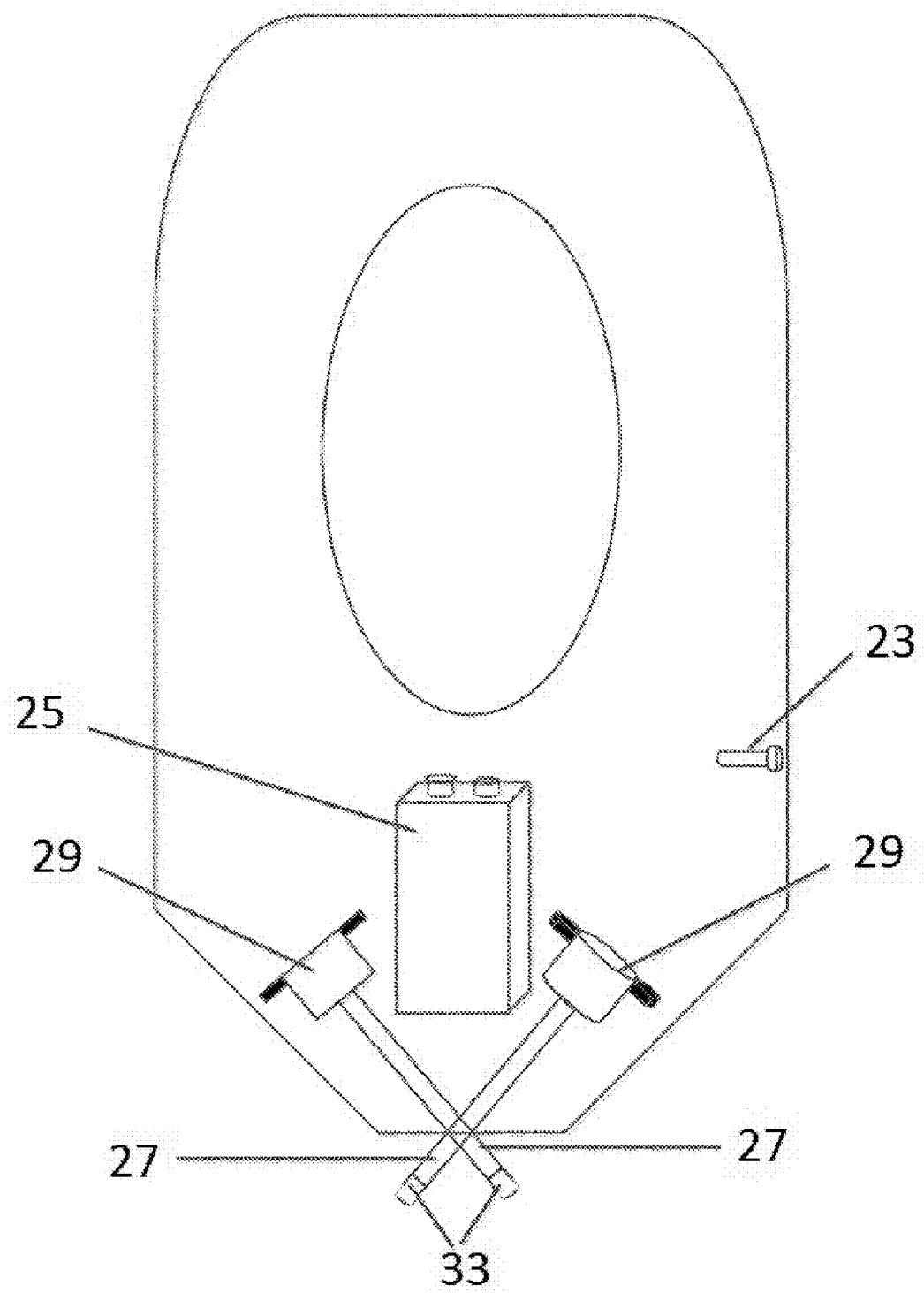
Figure 3:
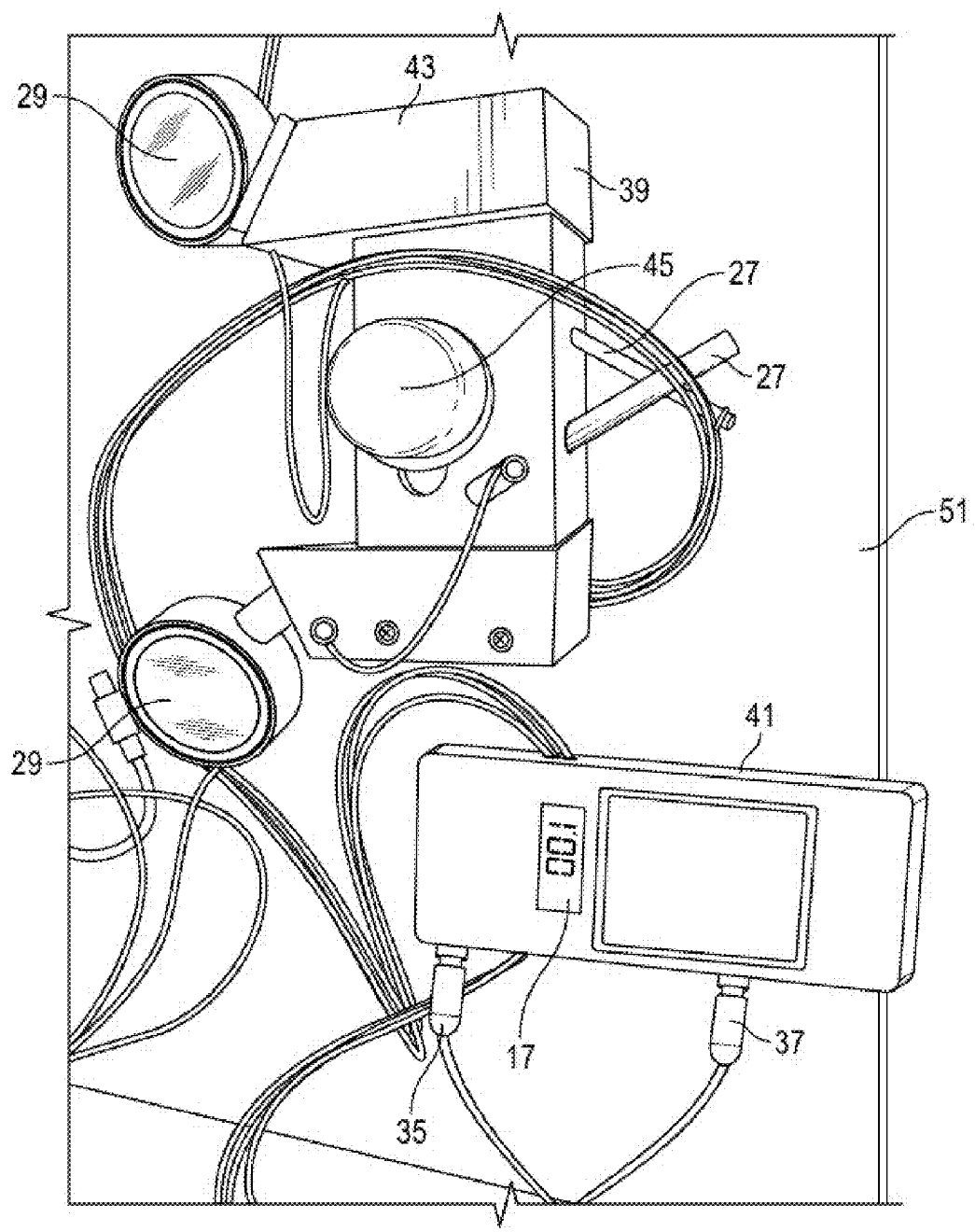
Figure 4:
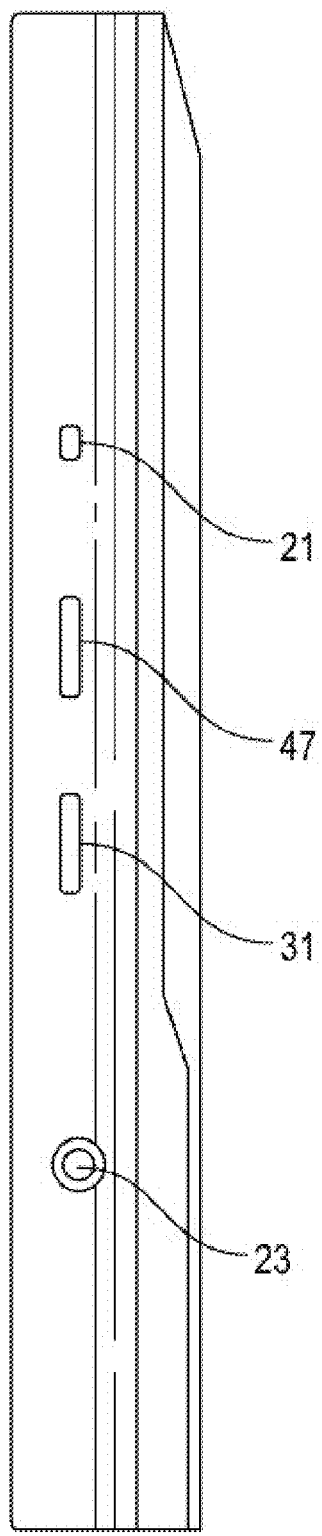
Figure 5:
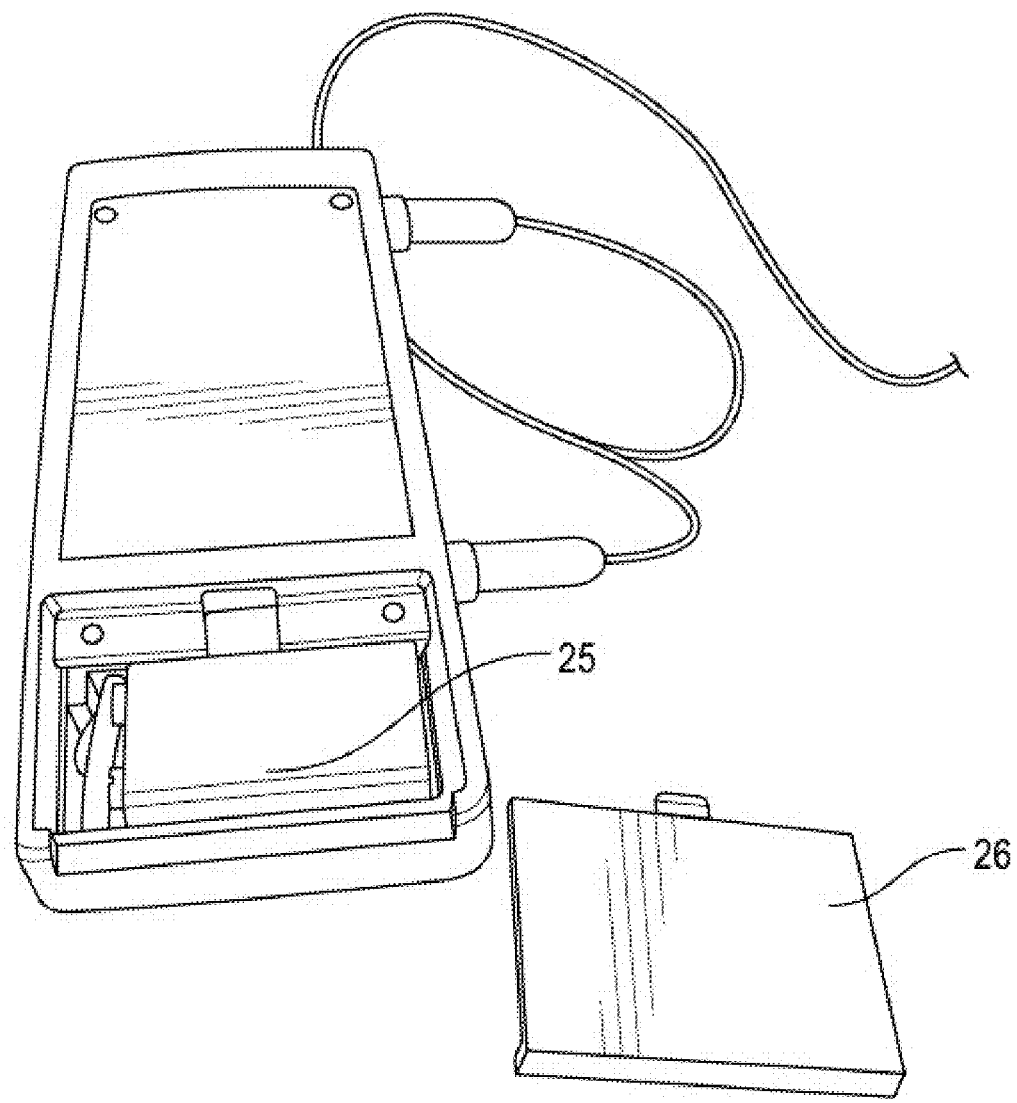

11—Switch to change digital display from microcurrent to force
13—Force LEDs—corresponding to right and left probes to display force from force gauges
15—LED bar graph displaying microcurrent.
17—Digital display
19—Mode select switch—changes between different calibrations.
21—Power switch
23—Earphone jack
25—Battery
26—Removable battery cover
27—Probes
29—Force gauges
31—Switches (up/down) for increasing/decreasing current, volume, or tone.
33—Probe tips
35 and 37—Leads, positive and negative, respectively
39—Mechanical component
41—Electronic component i.e., meter
43—Housing for mechanical component
45—Distance adjustment knob
47—Calibration knob for microcurrent measurement
49—Speaker volume control
51—Apparatus

DETAILED DESCRIPTION OF THE INVENTION

The expression, soft tissue injury, is used by health care personnel to denote injuries to muscles, tendons, ligaments, skin, fat, and other connective tissues that are occasionally the source of pain when they are injured.

Currently, there are no medical devices which specifically and objectively detect soft tissue injury.

Other diagnostic tests can objectively detect soft tissue injury, but they do so indirectly. MRIs, diagnostic Ultrasound, x-rays, and CT scans can detect edema that occurs secondary to a soft tissue injury, provided that there is a sufficient amount of edema from the injury. However, there is no simple, fast, low-cost, direct method on the market to detect soft tissue injury. The invention claimed here solves this problem.

The apparatus specifically and objectively detects soft tissue injury, is simple to use, provides a measurement in seconds, and will have a cost in the low thousands. The apparatus works by pairing electronic and mechanical components. The invention electronically measures microcurrent applied through the skin between two probes. Mechanically, force gauges measure the pressure on each probe, allowing for standardization of repeated tests. The microcurrent, measured in microohms, drops significantly over injured tissue, as much as 70%.

The claimed invention differs from what currently exists. The invention objectively detects soft tissue injury at a lower cost and in a shorter amount of time compared to MRI and diagnostic ultrasound. Also, MRI and other imaging techniques detect edema from injury, or possibly tears, not injured tissue which this invention detects.

MRI and diagnostic ultrasound indirectly detect tissue injury. Also, they are very expensive and can be slow.

This invention simply reports microcurrent numbers from repeated tests, standardized with the force gauges. It is fast, simple, and inexpensive, along with directly measuring tissue injury.

How the Invention Works:

When the invention is used, the mechanical 39 and electronic 41 components are connected by electrical leads 35 and 37. Alternatively, the mechanical and electronic components may be combined and connected within a single unit rather than separate mechanical and electronic components connected by leads.

First the microcurrent is calibrated to 100 microamps while shorting the two leads 35 and 37 with an external wire or sheet of copper. The probes 27 are then moved and applied directed to skin over a body part with an equal force on each probe, and the force being 0.5-1.5 pounds of pressure. Microcurrent then flows through the skin from probe to probe. The digital display 17 reports the microcurrent measurement and a speaker emits sounds proportional to the microcurrent. The force gauges 29 allow pressure to be consistent for repeated measurements.

In addition to the probes previously described, the invention can use twin probes, each the size of a pencil. The twin probes comprise an alternative mechanical component. Either the twin probes or the mechanical component are plugged into the electronic component. This is a redundancy for situations where the force gauged probes may not be sufficiently functional, say for a finger that is smaller than the separation distance of the housed probes.

Therefore, the purpose of this invention is to detect inflammation and/or injury by transmitting and measuring electrical current. The transmitted current is including, but not limited to direct current (DC), alternating current (AC), microcurrent, and other wave forms of electrical current. Measurement is of the following, but not limited to: microcurrent, electrical impedance, conductance, resistance, and complex impedance. The measurement is conducted through skin that has been stretched by methods including, but not limited to: mechanical stretch, angular probes, force applied at an angle, physical deformation, and conformational change.

A statistically significant average drop of 70% over a known injury occurs when compared to an adjacent uninjured area on the same subject or the same area on the opposite limb. It is important to note that this is a comparative number. Each individual person may have a different baseline microcurrent measurement, but only a 10%-30% change generally occurs over a particular body part with repeated measurements. For an injured area, the drop occurs when comparing measurements with the location of probes only shifted by an inch. When there is no injury, no statistically significant change is observed as a result of changing location by an inch.

The mechanism of this change is cellular damage as a result of hypoxia and electrical resistance diminishes as a result of ischemia and decreased blood flow. Also, cellular damage resulting from ischemia is caused by hypoxia, i.e., a lack of oxygen. Tissues surrounding a wound will experience ischemia and hypoxia due to the fact that the wound draws more of the blood circulation.

Statistically significant decreases in measured microcurrent are observed five minutes after induced ischemia, and decreases continue thirty seconds after the ischemic condition is removed. These effects on microcurrent magnitudes are due to cellular damage and not blood flow, as blood flow greatly increases in those thirty seconds.

Since there are few situations where an injured individual will also experience ischemia from external sources, the ischemic damage will be due to injury in a vast majority of cases. Thus, a decrease in microcurrent measurements over baseline measurements in the same subject is a method to detect areas of soft tissue injury.

The invention also serves as an outcome measurement to show healing by showing areas with decreased microcurrent rising over a treatment plan.

How to Make the Invention:

To make this invention, one must first assemble the electronic components. Electric current must be measured as it flows from one probe to the other by a meter 41, including but not limited to digital and analog meters. The probes must be conductive, including but not limited to metals. Current must only flow when an external surface connects the flow. There also must be a mechanism to connect the probes to allow for calibration. Mechanically, the probes must be attached to force gauges, including but not limited to electronic and mechanical gauges. These force gauges must measure the pressure applied to each probe. The probes are tipped with a disposable pad, including but not limited to cotton and cloth. An audio tone is produced, with the tone changing proportionally based on the quantity of microcurrent flow. The probes are mounted in a housing 43 to standardize the distance between probes 27 and the angle of the probes. Twin probes can also be attached to the microcurrent meter, as an alternative mechanical component which does not require a housing, but still allowing the microcurrent to be measured.

The meter and the probes are necessary for measurement of the microcurrent. The pads on the probes are optional, but are used for sanitary reasons. Improved force gauges and the housing, allowing for different angles, would improve the invention. Different sized probe housing units would also improve the invention, allowing for use on different sized body parts. Improved force gauges, able to break force into x, y, and z components would also improve the invention. Ideally, force gauges would allow a user to deliver force into the tested area and separating the probes, while eliminating any forces perpendicular to the plane of the probes.

There could be different housings for the probes, including but not limited to different sizes, force gauges, multiple force gauges, probe angles, material used for probes, material used for housing, handgrips and finger pads on the housing, comfort grips on the probes, different materials for wiring, and micromachined force sensors. There could also be different angles for the probes. For the electronic components, changes include but are not limited to microcurrent ranging from 0-1000 microamps, DC current, AC current, square wave current, medium frequency current, and different displays including but not limited to plasma, backlit LCD, non-backlit LCD, LED displays, and analog gauges. Current measurements changes could include but are not limited to electrical conductance, electrical resistance, complex impedance, electrical impedance, electrical current, microcurrent, phase angle, and reactance.

How to Use the Invention:

When the invention is used, the mechanical and electronic components are connected by electrical leads.

Cotton pads are inserted into the probes and wet with a conductive solution, generally 0.9% saline. First the microcurrent is calibrated to 100 microamps while shorting the two leads with an external conductive material, such as a wire or sheet of copper. The probes are then moved and applied directed to skin over a body part with and equal force on each probe, and the force being 0.5-1.5 pounds of pressure. Microcurrent then flows through the skin from probe to probe. The digital display reports the microcurrent measurement and the speaker. The force gauges allow pressure to be consistent for repeated measurements.

Measurements are taken over both injured and uninjured areas. A clinician should start at an uninjured area, take a reading, then move towards the suspected injured area an inch or so. As noted above, no significant decrease in microcurrent should occur with a displacement of 1 inch. Measurements should be taken across the entire suspected injured area. Microcurrent should decrease over the injured area, then rise again over healthy tissue. A clinician should draw lines with a pen around the injured area. Repeat this procedure until the injured area is completely demarcated. It is important to use consistent pressure on the probes with the repeated measurements.

Additionally: The invention is primarily for use in healthcare. Along with detection and demarcation of soft tissue injury, its uses can be beneficial in the medical-legal area. For example, it can detect whether or not someone has been injured in a rear end car accident or in a workplace incident. By detecting soft tissue injury, this invention can objectively say whether a person has been injured if the injury was not sufficient to cause tearing or fracture of bones or other tissue.

CONCLUSION

Although this invention has been described in detail with respect to its various components, it will be understood that many variations and modifications may be effected within the spirit and scope of the invention.

I claim:

1. An apparatus for detecting and locating regions of soft tissue injury in a patient to muscles, fascia, ligaments, and tendons comprising:
   an electronic component, said electronic component further comprising,
      a microcurrent display, a sound emitter,
      said electronic component further configured for calibration to 100 microamps,
   a mechanical component, said mechanical component further comprising a housing, a first probe, a second probe, a first force gauge, a second force gauge, a probe distance adjustment knob configured to set the distance between said first probe and said second probe, and wherein said mechanical component is adapted for successive measurements in which said first probe and said second probe are shifted on the patient's skin by approximately inch,
   wherein said electronic component and said mechanical component are electrically connected,
   wherein the first force gauge is configured to measure force applied, ranging from 0.5-1.5 pounds of pressure, to the first probe, and the second force gauge is configured to measure force applied, ranging from 0.5-1.5 pounds of pressure, to the second probe, and wherein the microcurrent display is configured to indicate the decrease in electrical current by the magnitude indicative of soft tissue injury,
   wherein the sound emitter is configured to emit a specific audible tone to indicate a decrease in electrical current of a magnitude indicative of soft tissue injury.

2. A method for detecting and locating regions of soft tissue injury in a patient to muscles, fascia, ligaments, and tendons using a microcurrent measuring apparatus comprising:
   calibrating an electronic component of the apparatus, said electronic component further comprised of a microcurrent display, and a sound emitter, with said electronic component being electrically connected to a positive lead and a negative lead, wherein a microcurrent is calibrated to 100 microamps while shorting said positive lead and said negative lead with an external conductor,
   determining a microcurrent value indicative of healthy tissue by applying a first probe and a second probe to the patient's skin over an uninjured area wherein the force applied by each probe is essentially equal and within 0.5-1.5 pounds of pressure, wherein said first probe and said second probe comprise a mechanical component, said mechanical component further comprising a housing, a first force gauge, a second force gauge, said first force gauge and said second force gauge configured to measure the force applied by each respective probe to the patient's skin, and a probe distance adjustment knob configured to set the distance between said first probe and said second probe, and wherein said mechanical and electronic components are connected by said positive and negative electrical leads,
   determining the microcurrent of skin over a region of suspected injured tissue by successively shifting the position of said first probe and said second probe on the patient's skin by approximately one inch, wherein said sound emitter is configured such that an audible tone is emitted if the microcurrent measured for the suspected injured tissue is less than the microcurrent measured for the healthy tissue by a magnitude indicative of tissue injury.

* * * * *